United States Patent
Fang et al.

(10) Patent No.: US 9,321,976 B1
(45) Date of Patent: Apr. 26, 2016

(54) HYDROXYALKYL SUBSTITUTED SUCCINIMIDES AND FUELS CONTAINING THEM

(71) Applicant: AFTON CHEMICAL CORPORATION, Richmond, VA (US)

(72) Inventors: Xinggao Fang, Midlothian, VA (US); Scott A. Culley, Midlothian, VA (US); Scott D. Schwab, Richmond, VA (US)

(73) Assignee: Afton Chemical Corporation, Richmond, VA (US)

( * ) Notice: Subject to any disclaimer, the term of this patent is extended or adjusted under 35 U.S.C. 154(b) by 0 days.

(21) Appl. No.: 14/855,631

(22) Filed: Sep. 16, 2015

(51) Int. Cl.
| | |
|---|---|
| *C10L 1/18* | (2006.01) |
| *C10L 10/08* | (2006.01) |
| *C10L 1/22* | (2006.01) |
| *C07D 207/325* | (2006.01) |
| *C10L 1/2383* | (2006.01) |

(52) U.S. Cl.
CPC .............. *C10L 10/08* (2013.01); *C07D 207/325* (2013.01); *C10L 1/22* (2013.01); *C10L 1/2383* (2013.01); *C10L 2200/0259* (2013.01); *C10L 2230/22* (2013.01); *C10L 2250/04* (2013.01); *C10L 2270/023* (2013.01)

(58) Field of Classification Search
CPC ......... C10L 10/08; C10L 1/22; C10L 1/2383; C10L 2200/0259; C10L 2230/22; C10L 2250/04; C10L 2270/023; C07D 207/325
See application file for complete search history.

(56) References Cited

U.S. PATENT DOCUMENTS

| | | | |
|---|---|---|---|
| 3,324,033 A | | 6/1967 | Knapp |
| 3,378,494 A | * | 4/1968 | Berger ............... B01F 17/0085 252/390 |
| 4,325,827 A | * | 4/1982 | Papay ................ C07D 207/412 44/347 |
| 4,997,456 A | * | 3/1991 | Malfer ............... C07D 207/412 44/347 |
| 5,122,616 A | | 6/1992 | Malfer |
| 5,554,768 A | | 9/1996 | Donges et al. |
| 7,182,795 B2 | | 2/2007 | Henly et al. |
| 8,425,627 B2 | | 4/2013 | Dietz et al. |
| 2003/0172584 A1 | | 9/2003 | Henly et al. |

FOREIGN PATENT DOCUMENTS

| | | | |
|---|---|---|---|
| GB | 984409 | * | 2/1965 |
| JP | 5504033 B2 | | 5/2014 |
| JP | 5504036 B2 | | 5/2014 |
| WO | 2014007377 A1 | | 1/2014 |

* cited by examiner

*Primary Examiner* — Cephia D Toomer
(74) *Attorney, Agent, or Firm* — Luedeka Neely Group, P.C.

(57) ABSTRACT

A fuel composition and method for reducing friction or wear and improving fuel economy in an engine. The fuel composition includes gasoline and from about 10 to about 750 ppm by weight based on a total weight of the fuel composition of a hydroxyalkyl hydrocarbyl-substituted succinimide compound having at least two hydroxyl groups attached to a tertiary nitrogen atom of a polyamino group through a hydrocarbyl link, wherein the hydroxyalkyl hydrocarbyl-substituted succinimide is devoid of primary and secondary amino groups.

19 Claims, No Drawings

HYDROXYALKYL SUBSTITUTED SUCCINIMIDES AND FUELS CONTAINING THEM

TECHNICAL FIELD

The disclosure is directed to use of a gasoline fuel composition that exhibits reduced engine friction or wear and improved fuel economy. In particular, the disclosure relates to hydroxyalkyl substituted succinimide additives that reduce friction or wear of engine parts and improve fuel economy of an engine.

BACKGROUND AND SUMMARY

Fuel compositions for vehicles are continually being improved to enhance various properties of the fuels in order to accommodate their use in newer, more advanced engines, such as in direct injected gasoline engines. Accordingly, fuel compositions typically include additives that are directed to certain properties that require improvement. For example, friction modifiers, such as fatty acid amides are added to fuel to reduce friction and wear in the fuel delivery systems of an engine. However, certain fatty acid amides may be unstable in additive packages for fuels at low storage temperatures and the performance of such fatty acid amides is less than desirable. Fuel additives may be passed into the oil sump during engine operation, so that a fuel additive that is also beneficial to the engine lubricant is desirable. While such additives may be beneficially added to the lubricant rather than the fuel, such additives are not effective for improving wear in fuel delivery systems. Also, such additives, when added to the fuel, rather than the lubricant, may reduce friction and wear in the piston ring zone of the engine and thus improve fuel economy. Accordingly, it is significantly more advantageous to include additives to fuels rather than to lubricants which can provide both improved fuel delivery system wear protection as well as improved fuel economy.

Partial esters of fatty acid and polyhydroxy alcohols such as glycerol monooleate (GMO) are known as friction modifiers for lubricant compositions. While GMO may improve fuel economy when added to a lubricant, GMO is unstable in additive packages for fuels and is known to cause an increase in intake valve deposits in gasoline engines.

Many other friction modifiers have been tried, however there remains a need for a friction modifier that is relatively stable in fuel additive packages, that is resistant to hydrolysis, that may be readily formulated into a fuel additive packages, that offers acceptable fuel economy benefits, and that provides wear protection to fuel delivery systems, among others characteristics. Accordingly, there continues to be a need for a fuel additive that is cost effective to manufacture and improves multiple characteristics of a fuel.

In accordance with the disclosure, exemplary embodiments provide a fuel composition and method for reducing wear and improving fuel economy in an engine. The fuel composition includes gasoline and from about 10 to about 750 ppm by weight based on a total weight of the fuel composition of a hydroxyalkyl hydrocarbyl-substituted succinimide compound having at least two hydroxyl groups attached to a tertiary nitrogen atom of a polyamino group through a hydrocarbyl link, wherein the hydroxyalkyl hydrocarbyl-substituted succinimide is devoid of primary and secondary amino groups.

In one embodiment of the disclosure, there is provided fuel composition for reducing friction or wear and improving engine fuel economy. The fuel composition includes gasoline and from about 10 to about 750 ppm by weight based on a total weight of the fuel composition of a reaction product that is derived from a hydrocarbyl-substituted succinic anhydride, a hydrocarbyl-substituted succinic ester, or hydrocarbyl-substituted succinic acid and a polyamine that is subsequently reacted with an epoxide compound. The reaction product is devoid of primary and secondary amino groups.

In another embodiment, there is provided a method for reducing friction or wear and improving fuel economy in an engine. The method includes fueling the engine with a fuel composition containing gasoline and from about 10 to about 750 ppm by weight based on a total weight of the fuel composition of a hydroxyalkyl hydrocarbyl-substituted succinimide compound having at least two hydroxyl groups attached to a tertiary nitrogen atom of a polyamino group through a hydrocarbyl link, wherein the hydroxyalkyl hydrocarbyl-substituted succinimide is devoid of primary and secondary amino groups, and operating the engine on the fuel composition.

An advantage of the fuel compositions and methods described herein is that the additive for the fuel composition may not only improve the friction or wear properties in an engine and fuel delivery system, but the additive may also be effective to improve fuel economy. An advantage of the hydroxyalkyl hydrocarbyl-substituted succinimide compound described above in a fuel additive package is that the additive package remains in a liquid state even at a temperature as low as −20° C. so that the entire additive package remains dissolved or suspended in the fuel composition. Another advantage of the hydroxyalkyl hydrocarbyl-substituted succinimide compound is that it is devoid of primary and secondary amino groups thereby improving the seal compatibility and demulsibility of fuel containing the reaction product.

In a further embodiment, the fuel composition contains from about 10 to about 750 ppm by weight, such as from 20 to about 500 ppm by weight, or from 30 to about 250 ppm by weight of the hydroxyalkyl hydrocarbyl-substituted succinimide compound based on a total weight of the fuel composition.

In another embodiment, an oil of lubricating viscosity contains from 0.05 to 5.0 wt. %, such as from 0.1 to 1.0 wt. %, or 0.15 to 0.5 wt. % of hydroxyalkyl hydrocarbyl-substituted succinimide compound based on the total weight of the oil composition.

Additional embodiments and advantages of the disclosure will be set forth in part in the detailed description which follows, and/or can be learned by practice of the disclosure. It is to be understood that both the foregoing general description and the following detailed description are exemplary and explanatory only and are not restrictive of the disclosure, as claimed.

DETAILED DESCRIPTION OF EXEMPLARY EMBODIMENTS

The fuel additive component of the present application may be used in a minor amount in a major amount of fuel and may be added to the fuel directly or added as a component of an additive concentrate to the fuel. A suitable fuel additive component for improving the operation of internal combustion engines as described herein may be made by reacting a hydrocarbyl-substituted dicarboxylic acylating agent with alkylamino alkanolamine to form an imide, wherein the reaction may optionally be conducted in an organic solvent, such as toluene at a temperature ranging from about 120° to about 200° C., such as about 140° to about 180° C. The resulting imide product is then reacted with an epoxide at a temperature ranging from about 40° to about 160° C. to provide a hydroxyalkyl hydrocarbyl-substituted imide compound having at least two hydroxyl groups attached to a tertiary nitrogen atom of a polyamino group through a hydrocarbyl link, wherein the hydroxyalkyl hydrocarbyl-substituted succinimide is devoid of primary and secondary amino groups. In one embodiment, the hydrocarbyl-substituted dicarboxylic acylating agent may be a reaction product of a hydrocarbon, generally a polyolefin substituted with a monounsaturated carboxylic acid reactant such as (i) α,β-monounsaturated $C_4$ to $C_{10}$ dicarboxylic acid such as fumaric acid, itaconic acid, maleic acid and anhydrides thereof.

In another embodiment, the hydrocarbyl-substituted dicarboxylic acylating agent may be a compound of the formula

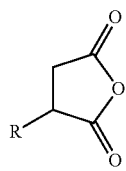

wherein R is a hydrocarbyl groups containing from 1 to 100 carbon atoms, such as 5 to 75 carbon atoms, or 10 to 22 carbon atoms. Examples of suitable hydrocarbyl-substituted acylating agents represented by the foregoing include, but are not limited to, tridecylsuccinic anhydride, pentadecylsuccinic anhydride, tetradecenylsuccinic anhydride, hexadecenylsuccinic anhydride, dodecylsuccinic anhydride, tetradecylsuccinic anhydride, hexadecylsuccinic anhydride, octadecenylsuccinic anhydride, tetrapropylene-substituted succinic anhydride, docosenylsuccinic anhydride, and mixtures thereof.

In one embodiment, R of foregoing structure represents an alkenyl group of 8 to 100 carbon atoms, more particularly about 12 to about 24 carbon atoms, that is an enoic (monounsaturated) or dienoic (two unsaturations) hydrocarbon chain. For example, the foregoing structure may represent an alkenyl succinic anhydride (ASA). In one embodiment, the hydrocarbyl-substituted acylating agent may be a single one of, or a mixture of, $C_{15}$-$C_{18}$ alkenyl succinic anhydrides. In another embodiment, the hydrocarbyl-substituted acylating agent may be a single one of, or a mixture of, $C_{20}$-$C_{24}$ alkenyl succinic anhydrides. As an example, a preferred ASA component for use in making the hydroxyalkyl hydrocarbyl-substituted succinimide disclosed herein may be a physical mixture or blend of hexadecenyl succinic anhydrides and octadecenyl succinic anhydrides, in all mixing ratios thereof.

As used herein, the term "hydrocarbyl group" or "hydrocarbyl" is used in its ordinary sense, which is well-known to those skilled in the art. Specifically, it refers to a group having a carbon atom directly attached to the remainder of a molecule and having a predominantly hydrocarbon character. Examples of hydrocarbyl groups include:
(1) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form an alicyclic radical);
(2) substituted hydrocarbon substituents, that is, substituents containing non-hydrocarbon groups which, in the context of the description herein, do not alter the predominantly hydrocarbon substituent (e.g., halo (especially chloro and fluoro), hydroxy, alkoxy, mercapto, alkylmercapto, nitro, nitroso, amino, alkylamino, and sulfoxy);
(3) hetero-substituents, that is, substituents which, while having a predominantly hydrocarbon character, in the context of this description, contain other than carbon in a ring or chain otherwise composed of carbon atoms. Hetero-atoms include sulfur, oxygen, nitrogen, and encompass substituents such as pyridyl, furyl, thienyl, and imidazolyl. In general, no more than two, or as a further example, no more than one, non-hydrocarbon substituent will be present for every ten carbon atoms in the hydrocarbyl group; in some embodiments, there will be no non-hydrocarbon substituent in the hydrocarbyl group.

As used herein, the term "major amount" is understood to mean an amount greater than or equal to 50 wt. %, for example from about 80 to about 98 wt. % relative to the total weight of the composition. Moreover, as used herein, the term "minor amount" is understood to mean an amount less than 50 wt. % relative to the total weight of the composition.

Amine Compound

According to the disclosure, the amine compound used to make the hydroxyalkyl hydrocarbyl-substituted succinimide compound described herein is a polyamine compound. Suitable polyamine compounds may include alkanol amine compounds containing at least two nitrogen atoms and at least one hydroxyl group. In one embodiment, the nitrogen containing moiety of the hydroxyalkyl hydrocarbyl-substituted succinimide compound is devoid of primary amino groups. In another embodiment, the nitrogen containing moiety of the hydroxyalkyl hydrocarbyl-substituted succinimide compound is devoid of primary and secondary amino groups. In one embodiment, the amine may contain from 2 to 8 nitrogen atoms.

In one embodiment, the polyamine comprises an aminoalkyl alkanolamine. Suitable aminoalkyl alkanolamines include, but are not limited to, aminoethyl ethanolamine, aminopropyl propanolamine, aminobutyl butanolamine, aminopropyl ethanolamine, aminobutyl ethanolamine, aminoethyl propanolamine, aminobutyl propanolamine, aminoethyl butanolamine, aminopropyl butanolamine, dihydroxyethyl ethylamine, dihydroxyethyl propylamine, and mixtures thereof.

In another embodiment, the amine may be selected from aminopropyl piperazine, aminoethyl piperazine, bis-aminoethyl piperazine, bis-aminopropyl piperazine, hydrocarbyl-substituted amino propylamine, and hydrocarbyl-substituted etheramino propylamine.

Other alkanol amine compounds may include, but are not limited to, 1-aminoethylamino-propanol-2, 1-aminoethylamino-butanol-2, 1-aminoethylamino-pentanol-2, 1-aminoethylamino-hexanol-2, 1-aninoethylamino-heptanol-2, 1-aminoethylamino-octanol-2, 1-aminoethylamino-butanol-3, 1-aminoethylamino-pentanol-3, 1-aminoethylamino-hexanol-3, 1-aminoethylamino-heptanol-3, 1-aminoethylamino-octanol-3, 1-aminoethylanmino-pentanol-4, 1-aminoethylamino-hexanol-4, 1-aminoethylamino-heptanol-4, 1-aminoethylamino-octanol-4, 1-aminopropylamino-propanol-2, 1-aminopropylamino-butanol-2, 1-aminopropylamino-pentanol-2, 1-aminopropylamino-hexanol-2, 1-amminopropylamino-heptanol-2, 1-aminopropylamino-octanol-2, 1-aminopropylamino-butanol-3, 1-aminopropylamino-pentanol-3, 1-aminopropylamino-hexanol-3, 1-aminopropylamino-heptanol-3, 1-aminopropylamino-octanol-3, 1-aminoethylamino-pentanol-4, 1-aminopropylamino-hexanol-4, 1-aminopropylamino-heptanol-4, 1-aminopropylamino-octanol-4, 1-aminobutylamino-propanol-2, 1-aminobutylamino-butanol-2, 1-aminobutylamino-pentanol-2, 1-aminobutylamino-hexanol-2, 1-aminobuylamino-pentanol-2, 1-aminobutylamino-octanol-2, 1-aminobutylamino-butanol-3, 1-aminobutylamino-pentanol-3, 1-aminobutylamino-hexanol-3, 1-aminobutylamino-heptanol-3, 1-aminobutylamino-octanol-3, 1-aminobutylamino-pentanol-4, 1-aminobutylamino-hexanol-4, 1-aminobutylamino-heptanol-4, 1-aminoethylamino-octanol-4, and the like.

Epoxide

A suitable epoxide may be selected from the following:
1,3-Butadiene diepoxide
Cyclohexene oxide
Cyclopentene oxide
Dicyclopentadiene dioxide
1,2,5,6-Diepoxycyclooctane
1,2,7,8-Diepoxyoctane
1,2-Epoxybutane
cis-2,3-Epoxybutane
3,4-Epoxy-1-butene
3,4-Epoxycyclohexylmethyl 3,4-epoxycyclohexanecarboxylate
1,2-Epoxydodecane
1,2-Epoxyhexadecane
1,2-Epoxyhexane
1,2-Epoxy-5-hexene
1,2-Epoxy-2-methylpropane
exo-2,3-Epoxynorbornane
1,2-Epoxyoctane
1,2-Epoxypentane
1,2-Epoxy-3-phenoxypropane
(2,3-Epoxypropyl)benzene
N-(2,3-Epoxypropyl)phthalimide
1,2-Epoxytetradecane
exo-3,6-Epoxy-1,2,3,6-tetrahydrophthalic anhydride
3,4-Epoxytetrahydrothiophene-1,1-dioxide
Isophorone oxide
Methyl-1,2-cyclopentene oxide
2-Methyl-2-vinyloxirane
α-Pinene oxide
Ethylene oxide
Propylene oxide
Polyisobutene oxide
cis-Stilbene oxide
Styrene oxide
Glycidol
Glycidol ethers
Tetracyanoethylene oxide
Tris(2,3-epoxypropyl) isocyanurate and combinations of two or more of the foregoing. A particularly suitable epoxide may be selected from ethylene oxide, propylene oxide and glycidol.

The hydroxyalkyl hydrocarbyl-substituted succinimide compound from the foregoing polyamines and an epoxide may be made by first contacting and mixing the polyamine with the hydrocarbyl-substituted acylating agent to form a succinimide from the polyamine. The succinimide may then be reacted with the epoxide in the reaction vessel. The mole ratio of acylating agent to polyamine in the first step of the reaction may range from about 1:0.8 to about 0.8:1. The mole ratio of epoxide to succinimide compound in the second step of the reaction may range from about 1:1 to about 3:1. The hydroxyalkyl hydrocarbyl-substituted succinimide compound may also be prepared in a one step reaction of hydroxyalkyl-substituted polyamine reacted with a hydrocarbyl-substituted acylating agent.

When the reaction is completed volatiles and unreacted reagents may be removed from the reaction product by heating the reaction product under vacuum. The product may be diluted with mineral oil, diesel fuel, kerosene, alcohol, or an inert hydrocarbon solvent to prevent the product from being too viscous, if necessary.

Of the foregoing, a particularly suitable hydroxyalkyl hydrocarbyl-substituted succinimide compound is a compound of the formula

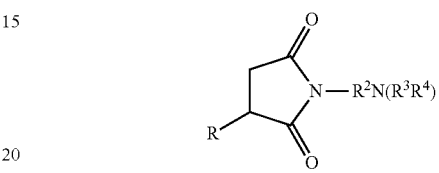

wherein R comprises a hydrocarbyl-substituted dicarboxyl group containing from about 9 to about 50 carbon atoms, such as from 12 to 22 carbon atoms, and each of $R^2$, $R^3$ and $R^4$ are selected from an alkyl group containing from 2 to 4 carbon atoms, an alkyl hydroxyl group containing 2 to 4 carbon atoms, and an alkyl group containing 2 to 4 carbon atoms and two hydroxyl groups, provided the succinimide compound contains at least two hydroxyl groups.

One or more additional optional compounds may be present in the fuel compositions of the disclosed embodiments. For example, the fuels may contain conventional quantities of octane improvers, corrosion inhibitors, detergents, cold flow improvers (CFPP additive), pour point depressants, solvents, demulsifiers, lubricity additives, additional friction modifiers, amine stabilizers, combustion improvers, dispersants, antioxidants, heat stabilizers, conductivity improvers, metal deactivators, carrier fluid, marker dyes, organic nitrate ignition accelerators, cyclomatic manganese tricarbonyl compounds, and the like. In some aspects, the compositions described herein may contain about 10 weight percent or less, or in other aspects, about 5 weight percent or less, based on the total weight of the additive concentrate, of one or more of the above additives. Similarly, the fuels may contain suitable amounts of conventional fuel blending components such as methanol, ethanol, dialkyl ethers, 2-ethylhexanol, and the like.

In one embodiment, a fuel additive package may contain the above described dihydroxyalkyl ether amine additive in combination with a carrier fluid and other ingredients selected from fatty amine ethoxylates; one or more detergents selected from Mannich bases, polyalkylamines, polyalkylpolyamines, polyalkenyl succinimides, and quaternary ammonium salt detergents. Quaternary ammonium salt detergents may be selected from compounds of the formula

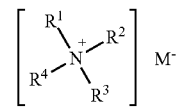

wherein each of $R^1$, $R^2$, $R^3$, and $R^4$ is selected from a hydrocarbyl group containing from 1 to 50 carbon atoms, wherein at least one and not more than three of $R^1$, $R^2$, $R^3$, and $R^4$ is a hydrocarbyl group containing from 1 to 4 carbon atoms and at least one of $R^1$, $R^2$, $R^3$, and $R^4$ is a hydrocarbyl group containing from 8 to 50 carbon atoms, $M^-$ is selected from the group consisting of carboxylates, nitrates, nitrides, nitrites, hyponitrites, phenates, carbamates, carbonates, and mixtures thereof, wherein the carboxylate is not an oxalate or formate; alkoxylated quaternary ammonium salts derived from epoxides, tertiary amines, and optional protonating agents; reaction products of amido amines or acylated amines containing at least one tertiary amino group and epoxides; reaction products of hydrocarbyl substituted anhydrides, tertiary amines and hydroxyl-containing epoxides; esterified quaternary ammonium salts derived from tertiary amines, epoxides, proton donors and anhydrides; reaction products of hydrocarbyl substituted compounds containing at least one tertiary amino group selected from $C_{10}$-$C_{30}$-alkyl or alkenyl-substituted amidopropyldimethylamines and $C_{12}$-$C_{200}$-alkyl or alkenyl-substituted succinic-carbonyldimethylamines and halogen substituted $C_2$-$C_8$ carboxylic acids, esters, amides, or salts thereof; and mixtures two or more of the foregoing detergents.

Suitable carrier fluids may be selected from any suitable carrier fluid that is compatible with the gasoline and is capable of dissolving or dispersing the components of the additive package. Typically the carrier fluid is a hydrocarbon fluid, for example a petroleum or synthetic lubricating oil basestock including mineral oil, synthetic oils such as polyesters or polyethers or other polyols, or hydrocracked or hydroisomerised basestock. Alternatively the carrier fluid may be a distillate boiling in the gasoline range. The amount of carrier fluid contained in the additive package may range from 10 to 80 wt %, preferably from 20 to 75 wt %,and more preferably from 30 to 60 wt % based on a total weight of the additive package. Such additive packages containing the dihydroxyalkyl ether amine additive, detergent and carrier fluid was found to remain fluid even at temperatures as low as −20 to −30° C.

In some embodiments of this application, the additives may be employed in amounts sufficient to reduce friction and/or wear in a fuel system or combustion chamber of an engine. For example, the gasoline fuels of this disclosure may contain, on an active ingredient basis, an amount of the hydroxyalkyl hydrocarbyl-substituted succinimide compound in the range of about 10 mg to about 500 mg of succinimide compound per Kg of fuel, such as in the range of about 20 mg to about 250 mg of per Kg of fuel or in the range of from about 30 mg to about 150 mg of the succinimide compound per Kg of fuel. The active ingredient basis excludes the weight of (i) unreacted components associated with and remaining in the product as produced and used, and (ii) solvent(s), if any, used in the manufacture of the product either during or after its formation.

The additives of the present application, including the hydroxyalkyl hydrocarbyl-substituted succinimide compound described above, and optional additives used in formulating the fuels of this invention may be blended into the base fuel individually or in various sub-combinations. In some embodiments, the additive components of the present application may be blended into the fuel concurrently using an additive concentrate, as this takes advantage of the mutual compatibility and convenience afforded by the combination of ingredients when in the form of an additive concentrate. Also, use of a concentrate may reduce blending time and lessen the possibility of blending errors.

The fuels of the present application may be applicable to the operation of gasoline engines. The engine include both stationary engines (e.g., engines used in electrical power generation installations, in pumping stations, etc.) and ambulatory engines (e.g., engines used as prime movers in automobiles, trucks, road-grading equipment, military vehicles, etc.).

Accordingly, aspects of the present application are directed to methods for reducing friction or wear in a gasoline engine or fuel system for a gasoline engine.

EXAMPLES

The following examples are illustrative of exemplary embodiments of the disclosure. In these examples as well as elsewhere in this application, all parts and percentages are by weight unless otherwise indicated. It is intended that these examples are being presented for the purpose of illustration only and are not intended to limit the scope of the invention disclosed herein.

Comparative Example 1

Glycerol Monooleate (GMO)

Comparative Example 2

Diethanolamine Fatty Amide Derived from Fatty Acid and Diethanol Amine

Comparative Example 3

Diethoxylated Cocoamine

Comparative Example 4

A $C_{15}$-$C_{18}$ alkylsuccinic anhydride (423 grams) was reacted with aminoethylethanolamine (132 grams) in the present of toluene (130 grams) at 160° C. The reaction was conducted until no more water was produced. The resulting reaction mixture was vacuum stripped at 130° C. to remove volatiles resulting in a viscous product.

Inventive Example 5

The reaction product of Comparative Example 4 (145 grams) was reacted with glycidol (25.5 grams) at 55° C. for 2.5 hours, then at 65° C. for 2.5 hours to give a product as a viscous oil.

Inventive Example 6

A $C_{20}$-$C_{24}$ alkylsuccinic anhydride (2000 grams) was reacted with aminoethylethanolamine (523 grams) in the present of toluene (100 grams) at 160° C. The reaction was conducted until no more water was produced. The resulting reaction mixture was vacuum stripped at 130° C. to remove volatiles resulting in a viscous product. The reaction product was then further reacted with 1 equivalent of ethylene oxide at 55° C. for 2.5 hours, then at 65° C. for 2.5 hours to give a product as a viscous oil.

Inventive Example 7

The succinimide from Inventive Example 6 (152 grams) was reacted with glycidol (22.5 grams) instead of ethylene oxide according to the procedure of Inventive Example 5 to give a product as a viscous oil.

Inventive Example 8

The reaction product of Comparative Example 4 (145 grams) was reacted with 1 equivalent of propylene oxide at 55° C. for 2.5 hours, then at 70° C. for 3 hours to give a product as a viscous oil.

Inventive Example 9

A $C_{12}$ alkylsuccinic anhydride (451 grams) was reacted with aminoethylethanolamine (175 grams) in the present of toluene (130 grams) at 160° C. The reaction was conducted until no more water was produced. The resulting reaction mixture was vacuum stripped at 130° C. to remove volatiles resulting in a viscous product. The reaction product was then further reacted with 3 equivalents of ethylene oxide at elevated temperatures under pressure until the ethylene oxide was consumed as evidenced by a pressure drop to give a product as a viscous oil.

In the following example, a friction test was conducted using a high frequency reciprocating rig (HFRR) under a 200 gram load with a stroke distance of 1 millimeter at 50 Hz according to diesel fuel test ASTM D6079 except that the test was conducted in gasoline fuel at 25° C. Fuel 1 is a gasoline fuel devoid of ethanol and Fuel 2 is a gasoline fuel containing 10 vol. % ethanol. The base fuel contained no additives. The treat rate of the additive and the results are given in the following table.

TABLE 1

Fuel HFRR data

| No. | Additive | Treat rate (ppm by wt.) | HFRR Wear (micrometer) Fuel 1 | HFRR Wear (micrometer) Fuel 2 |
|---|---|---|---|---|
| 1 | Base fuel (no additives) | 0 | 800 | 750 |
| 2 | Base fuel plus Mannich base detergent package at 280 ppm by weight | — | 790 | — |
| 3 | No. 2 plus additive of Comparative Ex. 2 | 160 | 750 | 740 |
| 4 | No. 2 plus additive of Comparative Ex. 3 | 160 | 475 | 695 |
| 5 | No. 2 plus additive of Comparative Ex. 4 | 160 | 400 | — |
| 6 | No. 2 plus additive of Inventive Ex 5 | 160 | 270 | 510 |
| 7 | No. 2 plus additive of Inventive Ex 6 | 160 | 412 | 615 |

As shown by the foregoing results in Table 1, the additive of Inventive Examples 5-6 (Nos. 6-7) provided significant and unexpected wear reduction compared to the base fuel (No. 1), a conventional fuel additive package plus base fuel (No. 2) and the additives of Comparative Examples 2 and 3 (Nos. 3-4). Inventive Examples gave comparable or better wear protection than Comparative Example 4 (No. 5).

In the following example, the storage stability of a conventional gasoline fuel additive package containing Inventive Examples 5-8 was compared to an additive package containing Comparative Example 3. All of the samples in the following table contained 53.85 wt. % of the conventional gasoline fuel additive package and the amount of additive and solvent shown.

TABLE 2

Storage Stability at −20° C.

| No. | Additive | Treat rate (wt.%) | Solvent Wt.% | 1 day | 1 week |
|---|---|---|---|---|---|
| 1 | Comparative Ex. 3 in aromatic solvent | 30.77 | 15.38 | frozen | — |
| 2 | Comparative Ex. 3 in mixed aromatic solvent/ 2-ethylhexanol | 30.77 | 7.69/ 7.69 | frozen | — |
| 3 | Inventive Ex. 5 in 2-ethylhexanol | 30.77 | 15.38 | liquid | liquid |
| 4 | Inventive Ex. 6 in aromatic solvent | 30.77 | 15.38 | liquid | liquid |
| 5 | Inventive Ex. 7 in 2-ethylhexanol | 30.77 | 15.38 | liquid | liquid |
| 6 | Inventive Ex. 8 in 2-ethylehexanol | 30.77 | 15.38 | liquid | liquid |
| 7 | Inventive Ex. 9 in e-ethylhexanol | 30.77 | 15.38 | liquid | liquid |

As shown by the foregoing examples, the Inventive Examples (5-9) (Runs 3-7) exhibited significantly improved low temperature storage stability in a fuel additive package compared to Comparative Example 3 (Runs 1-2) which did not remain liquid in the additive package at −20° C. Accordingly, fuel containing the additive of Inventive Examples 5-9 is expected to provide improved wear reduction and fuel economy increase without drawbacks of other fuel additives that may provide comparable performance in gasoline.

Modified Sequence VI E Dynamometer Testing

A modified Sequence VIE testing was carried out using a General Motors 3.6 L (LY7) V6, 4-cycle engine equipped with dual overhead camshafts and having four valves per cylinder and also equipped with a dual stage Plenum induction manifold with 94×85.6 mm bore & stroke with 10.2:1 compression ratio. The test fuel was the Sequence VI E reference fuel and the motor oil was a formulated SAE 0W-20 passenger car engine oil containing all of the standard engine oil components, but containing no friction modifiers. The friction modifier to be tested was solubilized in the Sequence VIE motor oil to provide the concentration of friction modifier of 0.125 wt. % in the crankcase lubricant. The engine was operated with the baseline engine oil at 1500 rpm, a torque of 150 N-m, an oil temperature of 115° C. and a coolant temperature of 109° C. until the temperatures stabilized. The brake specific fuel consumption (BSFC) was measured for approximately one hour after stabilization. The top-treat containing the friction modifier was then added to the crankcase. Upon the addition of the top-treat, the BSFC decreased over the course of about five minutes. The engine was run until the BSFC was stabilized, the fuel consumption was then measured for approximately one hour. The fuel economy improvement was calculated from the average BSFC before and after the addition of the friction modifier top-treat.

TABLE 3

Fuel Economy Increase

| Run No. | Friction Modifier in engine oil | % Fuel Economy Increase |
|---|---|---|
| 1 | Base oil, plus no top treat additive | 0 |
| 2 | Base oil, plus Comparative Example 1 | 0.42 |
| 3 | Base oil, plus Comparative Example 2 | 0.24 |
| 4 | Base oil plus Inventive Example 5 | 0.31 |
| 5 | Base oil plus Inventive Example 6 | 0.90 |

TABLE 3-continued

Fuel Economy Increase

| Run No. | Friction Modifier in engine oil | % Fuel Economy Increase |
|---|---|---|
| 6 | Base oil plus Inventive Example 7 | 0.49 |
| 7 | Base oil plus Inventive Example 9 | 0.53 |

As shown by the foregoing examples, Inventive Examples 5-7 and 9 provided a significant increase in fuel efficiency compared to a base oil containing no top treat additive. While Comparative Examples 1 provided good fuel economy increase in a lubricant composition, as set forth above, GMO (Comparative Example 1) is well known to be unstable in additive packages for fuels and is known to cause an increase in intake valve deposits in gasoline engines.

It is noted that, as used in this specification and the appended claims, the singular forms "a," "an," and "the," include plural referents unless expressly and unequivocally limited to one referent. Thus, for example, reference to "an antioxidant" includes two or more different antioxidants. As used herein, the term "include" and its grammatical variants are intended to be non-limiting, such that recitation of items in a list is not to the exclusion of other like items that can be substituted or added to the listed items For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

What is claimed is:

1. A fuel composition for improving fuel economy and reducing wear in an engine, wherein the fuel composition comprises gasoline and from about 10 to about 750 ppm by weight based on a total weight of the fuel composition of a hydroxyalkyl hydrocarbyl-substituted succinimide compound having at least two hydroxyl groups attached to a tertiary nitrogen atom of a polyamino group through a hydrocarbyl link, wherein the hydroxyalkyl hydrocarbyl-substituted succinimide is devoid of primary and secondary amino groups.

2. The fuel composition of claim 1, wherein the engine comprises a fuel injected gasoline engine.

3. The fuel composition of claim 1, wherein the polyamino group is derived from an aminoalkyl alkanolamine.

4. The fuel composition of claim 3, wherein the aminoalkyl alkanolamine is selected from the group consisting of aminoethylethanol amine, aminopropylpropanol amine, aminobutylbutanol amine, aminopropylethanol amine, aminobutylethanol amine, aminoethylpropanol amine, aminobutylpropanol amine, aminoethylbutanol amine, aminopropylbutanol amine, aminopropyl piperazine, aminoethyl piperazine, hydrocarbylamino propylamine, hydrocarbyletheramino propylamine, and mixtures thereof.

5. The fuel composition of claim 1, wherein the fuel composition contains from about 40 to about 160 ppm by weight of the hydroxyalkyl hydrocarbyl-substituted succinimide compound based on a total weight of the fuel composition.

6. The fuel composition of claim 1, wherein the hydrocarbyl group of the hydrocarbyl-substituted succinimide compound contains from 8 to 22 carbon atoms.

7. A fuel composition for reducing friction or wear and improving engine fuel economy, comprising gasoline and from about 10 to about 750 ppm by weight based on a total weight of the fuel composition of a reaction product that is derived from a hydrocarbyl-substituted succinimide compound and a polyamine that is subsequently reacted with an epoxide compound, wherein the reaction product is devoid of primary and secondary amino groups.

8. The fuel composition of claim 7, wherein the epoxide is selected from the group consisting of ethylene oxide, propylene oxide and glycidol.

9. The fuel composition of claim 7, wherein the fuel composition contains from about 40 to about 160 ppm by weight of the reaction product based on a total weight of the fuel composition.

10. The fuel composition of claim 7, wherein the hydrocarbyl group of the hydrocarbyl succinimide compound contains from 12 to 24 carbon atoms.

11. The fuel composition of claim 1, wherein the polyamino group contains from 2 to 8 nitrogen atoms.

12. A method for reducing friction or wear and improving fuel economy in an engine, comprising fueling the engine with a fuel composition comprising gasoline and from about 10 to about 750 ppm by weight based on a total weight of the fuel composition of a hydroxyalkyl hydrocarbyl-substituted succinimide compound having at least two hydroxyl groups attached to a tertiary nitrogen atom of a polyamino group through a hydrocarbyl link, wherein the hydroxyalkyl hydrocarbyl-substituted succinimide is devoid of primary and secondary amino groups, and operating the engine on the fuel composition.

13. The method of claim 12, wherein the engine comprises a fuel injected gasoline engine.

14. The method of claim 12, wherein the polyamino group is derived from an aminoalkyl alkanolamine.

15. The method of claim 14, wherein the aminoalkyl alkanolamine is selected from the group consisting of aminoethyl ethanolamine, aminopropyl propanolamine, aminobutyl butanolamine, aminopropyl ethanolamine, aminobutyl ethanolamine, aminoethyl propanolamine, aminobutyl propanolamine, aminoethyl butanolamine, aminopropyl butanolamine, aminopropyl piperazine, aminoethyl piperazine, bis-aminopropyl piperazine, bis-aminoethyl piperazine, hydrocarbylamino propylamine, hydrocarbyletheramino propylamine, and mixtures thereof.

16. The method of claim 12, wherein the fuel composition contains from about 80 to about 120 ppm by weight of the hydroxyalkyl hydrocarbyl-substituted succinimide compound based on a total weight of the fuel composition.

17. The method of claim 12, wherein the hydrocarbyl group of the hydrocarbyl succinimide compound contains from 10 to 50 carbon atoms.

18. A fuel additive package comprising a hydroxyalkyl hydrocarbyl-substituted succinimide compound having at least two hydroxyl groups attached to a tertiary nitrogen atom of a polyamino group through a hydrocarbyl link, wherein the hydroxyalkyl hydrocarbyl-substituted succinimide is devoid of primary and secondary amino groups, a detergent and a carrier fluid.

19. The fuel additive package of claim 18, wherein the additive package remains fluid at temperatures as low as −20° C. or lower.

\* \* \* \* \*